United States Patent [19]

Krishnan et al.

[11] 4,320,049
[45] Mar. 16, 1982

[54] FLAME RETARDING AGENTS FOR POLYCARBONATES

[75] Inventors: Sivaram Krishnan; Russell P. Carter, Jr., both of New Martinsville, W. Va.; Robert D. Kroshefsky, Aliquippa, Pa.

[73] Assignee: Mobay Chemical Corporation, Pittsburgh, Pa.

[21] Appl. No.: 167,971

[22] Filed: Jul. 14, 1980

[51] Int. Cl.³ ............... C07D 209/48; C08K 5/34
[52] U.S. Cl. .................... 524/94; 252/609; 260/326 E; 260/326 S
[58] Field of Search ............ 260/45.8 NB, 326 E, 260/326 S, 45.7 SF; 252/609

[56] References Cited

U.S. PATENT DOCUMENTS

| | | | |
|---|---|---|---|
| 3,313,763 | 4/1967 | Creighton et al. | 260/45.8 NB |
| 3,535,300 | 10/1970 | Gable | 260/45.7 RL |
| 3,663,495 | 5/1972 | Michael et al. | 260/45.8 NB |
| 3,775,367 | 11/1973 | Nouverné | 260/45.9 R |
| 3,801,533 | 4/1974 | Tetenbaum et al. | 260/45.8 NB |
| 3,868,388 | 2/1975 | Dotson, Jr. et al. | 260/326 N |
| 3,873,567 | 3/1975 | Cyba | 260/45.8 NB |
| 3,915,930 | 10/1975 | Dotson, Jr. et al. | 260/45.8 N |
| 3,919,167 | 11/1975 | Mark | 260/45.8 N |
| 3,923,734 | 12/1975 | Dotson, Jr. et al. | 260/45.75 B |
| 3,933,734 | 1/1976 | Mark et al. | 260/45.7 SF |
| 3,940,366 | 2/1976 | Mark | 260/45.7 SF |
| 3,971,756 | 7/1976 | Bialous et al. | 260/45.7 R |
| 4,001,179 | 1/1977 | Richter et al. | 260/45.75 B |
| 4,003,862 | 1/1977 | Albright | 260/2.5 AJ |
| 4,066,618 | 1/1978 | Mark | 260/45.85 T |
| 4,067,846 | 1/1978 | Mark | 260/45.9 KA |
| 4,069,201 | 1/1978 | Mark | 260/45.95 R |
| 4,073,768 | 2/1978 | Mark | 260/45.7 S |
| 4,075,164 | 2/1978 | Mark | 260/45.7 S |
| 4,087,441 | 5/1978 | Lee | 260/326 N |
| 4,093,589 | 6/1978 | Factor et al. | 260/45.75 B |
| 4,208,489 | 6/1980 | Schmidt et al. | 260/45.8 NB |

FOREIGN PATENT DOCUMENTS 53-24393 3/1978 Japan.
1287934 9/1972 United Kingdom.

Primary Examiner—John Kight, III
Assistant Examiner—R. A. White
Attorney, Agent, or Firm—Gene Harsh; Lawrence S. Pope; Aron Preis

[57] ABSTRACT

A sufficient amount of a novel halogenated aromatic imide sulfonate, represented by the structural formula:

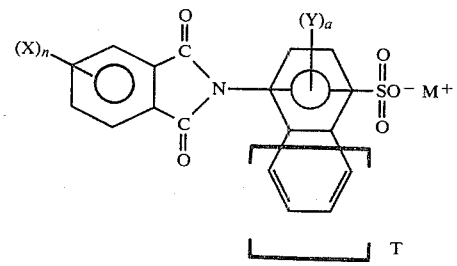

wherein X is a halogen, n is 1 to 4, Y is a lower alkyl having 1 to 4 carbon atoms, a halogen or a hydrogen atom, "a" is 0 to 4, M is an alkali metal and T is either 0 or 1, is incorporated into an aromatic polycarbonate to provide flame resistance thereto.

8 Claims, No Drawings

FLAME RETARDING AGENTS FOR POLYCARBONATES

BACKGROUND OF THE INVENTION

1. Field of the Invention

This invention relates to polycarbonates and more particularly to flame retarding agents for polycarbonates.

2. Description of the Prior Art

Polycarbonates derived from reactions involving aromatic dihydroxy compounds and carbonic acid derivatives have found extensive commercial application because of their excellent mechanical and physical properties. These thermoplastic polymers are particularly suited for the manufacture of molded products requiring impact strength, rigidity, toughness, thermal and dimensional stability as well as excellent electrical properties.

However, these polymers exhibit a brief though definite burning time when contacted with an open flame and do not meet certain specified requirements for flammability resistance in applications where high temperatures and/or exposure to fire may be encountered. In addition, stabilizers or other functional additives which are normally used in polycarbonates will further modify the burning characteristics of the plastic, to make them unacceptable where a certain flame retardance requirement is specified.

Also, stabilizers and functional additives such as monomeric phosphates, phosphoric acid esters and thiophosphoric acid esters containing halogenated alkyl radicals have been incorporated into polymers to increase their flame resistant properties. Metal salts have also been utilized to provide flame retardance characteristics to polycarbonates. Further, in aromatic polycarbonate resins some of the phenolic diols used in the production thereof have chlorine or bromine atoms substituted on the aromatic ring to provide flame resistant characteristics to the final polycarbonate.

Illustrative of the sulfonic acid salts and of metal salts are those disclosed in U.S. Pat. Nos. 3,775,367; 4,067,846; 4,073,768; 4,075,164; 4,066,618; 4,069,201; 4,093,589; 3,971,756; 3,933,734; 3,940,366, and 3,919,167, all incorporated herein by reference.

Some of these flame retardants, however, in order to be effective, are added in relatively large amounts such as to adversely effect some of the desirable properties of the base resin. For example, both the impact strength and the hydrolytic stability are compromised upon addition of large quantities of salt. Further, many of these flame retarding salts are susceptible to volatilization at the high molding temperatures of polycarbonates, necessitating thus the addition of excess amounts of salt which in turn bring about haze and loss of transparency. Since there is no uniformity of processing conditions among molders, it becomes difficult, if not impossible, to regulate the ultimate amount of salt incorporated into the polycarbonate.

Flame retardants incorporating a phthalimide group have been disclosed in, for instance, British Pat. No. 1,287,934 and U.S. Pat. Nos. 3,873,567; 3,923,734; 3,915,930; 3,868,388; 4,087,441; 4,001,179 and 4,003,862.

In accordance with the present invention a sulfonate salt is provided which is characterized by low volatility under normal polycarbonate processing conditions, which imparts improved flame resistance to polycarbonates even at low concentrations.

BRIEF DESCRIPTION OF THE INVENTION

The invention is directed to a halogenated imide sulfonate salt represented by the structural formula:

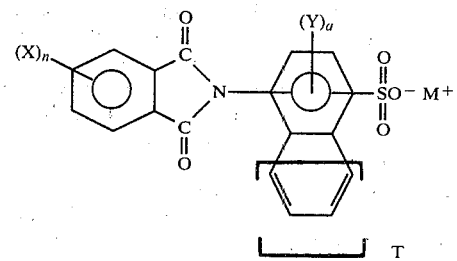

wherein X is a halogen atom, n equals 1 to 4, Y is a lower alkyl having 1 to 4 carbon atoms or a halogen atom, "a" is 0 to 4, M is an alkali metal and T is either 0 or 1 which is a flame retarding agent for polycarbonate resins.

A flame resistant polycarbonate composition comprising polycarbonate resin and the halogenated aromatic imide sulfonate is disclosed.

DETAILED DESCRIPTION OF THE INVENTION

When used herein "polycarbonate resin" means the neat resin without additives; "polycarbonate" means both the formulated polycarbonate resin with additives therein and also the final molded plastic product.

The polycarbonate resins useful in practice of the invention are produced by reacting phenolic dihydroxy compounds such as di-(monohydroxyaryl)-alkanes or dihydroxybenzenes and substituted dihydroxybenzenes with derivatives of the carbonic acids such as carbonic acid diesters, phosgene, bis-chloro-carbonic acid esters of di-(monohydroxyaryl)-alkanes and the bis-chlorocarbonic acid esters of the dihydroxybenzenes and the substituted dihydroxybenzenes.

The two aryl residues of the di-(monohydroxyaryl)-alkanes applied according to the invention can be alike or different. The aryl residues can also carry substituents which are not capable of reacting in the conversion into polycarbonates, such as halogen atoms or alkyl groups, for example, the methyl, ethyl, propyl, or tert.-butyl groups. The alkyl residue of the di-(monohydroxyaryl)-alkanes linking the two benzene rings can be an open chain or a cycloaliphatic ring and may be substituted, if desired, for example, by an aryl residue.

Suitable di-(monohydroxyaryl)-alkanes are, for example, (4,4'-dihydroxy-diphenyl)-methane, 2,2'-(4,4'-dihydroxy-diphenyl)-propane, 1,1-(4,4'-dihydroxy-diphenyl)cyclohexane, 1,1-(4,4'-dihydroxy-3,3'-dimethyl-diphenyl)cyclohexane, 1,1-(2,2'-dihydroxy-4,4'-dimethyl-diphenyl)butane, 2,2-(2,2'-dihydroxy-4,4'-di-tert.-butyl-diphenyl)propane or 1,1-(4,4'-dihydroxydiphenyl)-1-phenyl-ethane; furthermore, methane derivatives which carry besides two hydroxyaryl groups an alkyl residue with at least two carbon atoms and a second alkyl residue with one or more carbon atoms, such as 2,2-(4,4'-dihydroxy-diphenyl)-butane, 2,2-(4,4'-dihydroxy-diphenyl)-pentane (melting point 149°–150° C.), 3,3-(4,4'-dihydroxy-diphenyl)-pentane, 2,2-(4,4'-dihydroxy-diphenyl)-hexane, 3,3-(4,4'-dihydroxydiphenyl)hexane, 2,2-(4,4'-dihydroxy-diphenyl)-4-methyl-pentane, 2,2-(4,4'-dihydroxy-diphenyl)-heptane, 4,4-(4,4'-dihydroxy-diphenyl)-heptane (melting point 148°-149° C.) or 2,2-(4,4'-dihydroxy-diphenyl)-tri-decane. Suitable di-(monohydroxyaryl)-alkanes, the two aryl residues of which are different, are, for example, 2,2-(4,4'-dihydroxy-3-methyl-diphenyl)propane and 2,2-(4,4'-dihydroxy-3-methyl-3'-isopropyldiphenyl)-butane. Suitable di-(monohydroxyaryl)-alkanes, the aryl residues of which carry halogen atoms are, for instance, 2,2-(3,3',5,5'-tetra-chloro-4,4'-dihydroxy-diphenyl)-propane, 2,2-(3,3',5,5'-tetra-bromo-4,4'-dihydroxy-diphenyl)-propane, (3,3'-dichloro-4,4'-dihydroxy-diphenyl)-methane and 2,2'-dihydroxy-5,5'-difluorodiphenyl-methane. Suitable di-(monohydroxyaryl)-alkanes, the alkyl residue of which, linking the two benzene rings, is substituted by an aryl residue are, for instance, (4,4'-dihydroxy-diphenyl)-phenyl-methane and 1,1-(4,4'-dihydroxy-diphenyl)-1-phenyl-ethane.

Suitable dihydroxybenzenes and substituted dihydroxybenzenes are hydroquinone, resorcinol, pyrocatechol, methyl hydroquinone and the like. Other suitable dihydroxy aromatic compounds are 4,4'-dihydroxybiphenyl, 2,2'-dihydroxy-biphenyl, dihydroxynaphthalene, dihydroxyanthracene and compounds represented by the structural formula:

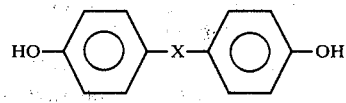

wherein X is S,

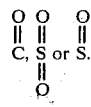

In order to obtain special properties, mixtures of various di-(monohydroxyaryl)-alkanes can also be used, thus mixed polycarbonate resins are obtained. By far the most useful polycarbonate resins are those based on bis(4-hydroxyaryl)-alkanes and more particularly bisphenol A [2,2-(4,4'-dihydroxy-diphenyl)-propane].

In addition, minor amounts of tri- or greater functional aromatic compounds may be used to branch the polycarbonate resins. Some examples of compounds with three or more than three phenolic hydroxyl groups which can be used are phloroglucinol; 2,4-dimethyl-2,4,6-tris(4-hydroxyphenyl)heptane; 2,4,6-trimethyl-2,4,6-tris(4-hydroxyphenyl)heptane; 1,4,5-tris(4-hydroxyphenyl)benzene; 1,1,1-tris(4-hydroxyphenyl)ethane; tris(4-hydroxyphenyl)phenylmethane; 2,2-bis[4,4'-bis(4-hydroxyphenyl)cyclohexyl]propane; 2,4-bis(4-hydroxyphenylisopropyl)phenol; 2,6-bis(2-hydroxy-5-methylbenzyl)-4-methylphenol; 2-(4-hydroxyphenyl)-2-(2,4-dihydroxyphenyl)propane; tetrakis(4-hydroxyphenyl)methane; tetrakis(4-(4-hydroxyphenylisopropyl)phenoxy)methane; and 1,4-bis((4',4''-dihydroxytriphenyl)-methyl)-benzene. Some of the other functional compounds are 2,4-dihydroxybenzoic acid, trimellitic acid, cyanuric chloride and 3,3-bis(4-hydroxyphenyl)-2-oxo-2,3-dihydroindole.

The polycarbonate resins are those having a weight average molecular weight from 10,000 to 200,000 and preferably a melt flow range of 1 to 24 g/10 min. (ASTM D-1238, Condition O) and are prepared by methods known to those skilled in the art, and more particularly by methods disclosed in U.S. Pat. Nos. 3,028,365; 2,999,846; 3,248,414; 3,153,008; 3,215,668; 3,187,065; 2,964,974; 2,970,137; 2,991,273; and 2,999,835, all incorporated herein by reference.

The halogenated aromatic imide sulfonate salts of the invention can be represented by the preferred structural formula:

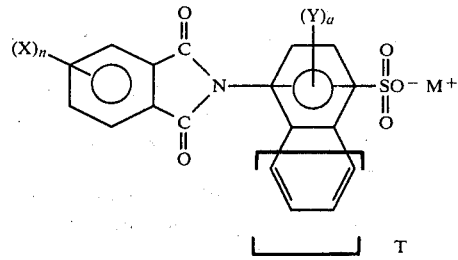

wherein X is a halogen, n is between 1 and 4, Y is a lower alkyl having 1 to 4 carbon atoms or may be a halogen, "a" is 0 to 4, M is an alkali metal metal and T is either 0 or 1. Typically the halogens which may be X or Y are fluorine, bromine, chlorine or iodine and most preferably chlorine or bromine. Preferably, "a" is equal to 0. Although both alkali and alkali earth metals are suitable in the practice of the invention, the former are preferred. The alkali metals are typically sodium or potassium and more preferably sodium.

The halogenated aromatic imide sulfonate may be prepared by reacting an aromatic halo-orthocarboxylic acid and/or the anhydride thereof with a substituted or unsubstituted alkali metal salt of sulfanilic acid in equal molar quantities. The reaction is performed at elevated temperature in a suitable solvent to form a halogenated aromatic imide sulfonate salt useful in the practice of the invention.

The halogenated aromatic imide sulfonate salts of this invention may be incorporated into the polycarbonate at a level of 0.01 to about 1% by weight and preferably from about 0.1 to 0.75% by weight based upon the weight of the polycarbonate resin.

In addition to the halogenated aromatic imide sulfonate a minor amount of a polytetrafluoroethylene polymer may also be incorporated into the polycarbonate as a drip suppressant. Both fibrillating and nonfibrillating fluorinated polyolefin polymers may be used which are typically prepared from the polymerization of fluorinated olefins such as fluorinated ethylene and fluorinated propylene and most desirably tetrafluoroethylene. The total fluorinated polyolefin polymer concentration in the polycarbonate is about 0.01 to about 3% by weight based on the total weight of the polycarbonate resin and more preferably 0.01 to 2%.

In addition to the previously recited constituents other materials known to those skilled in the art may be used to impart particular properties. For example, pigments or dyes may be added in order to form opaque or colored molded products. In the case of opaque products, titanium dioxide is predominantly used to opacify the polycarbonate to form a white molded product. If a colored product is desired, pigments such as chrome yellows and oranges, and chrome greens may be added to provide various colors to the article. Also oil soluble dyes may be incorporated into the polycarbonate to impart color to the final molded article. In order to color the polycarbonate, minimum amounts of colorant, i.e., 0.01 to 10 grams colorant per pound polycarbonate, may be required.

Preferably, the polycarbonate prepared in accordance with the invention exhibit what is known as a UL 94 V-0 rating. The UL 94 test is conducted as follows:

Test specimens of polycarbonate are molded into bars having dimensions of 5.00×0.5×1/16 (or ⅛) inches. The bars are mounted vertically so that the bottom of the test specimen is 12 inches above a swatch of surgical cloth. Each test bar is individually ignited for two successive 10 second ignitions and the burning characteristics after each ignition are noted and the sample is rated. A Bunsen burner is used to ignite the sample with a ¾" (10 mm) blue flame from natural gas having approximately 1,000 BTU per cubic foot heat content.

The UL 94 V-0 classification exemplifies the following properties in materials tested in accordance with the UL 94 specification. Polycarbonates within this class have no samples which burn for more than 10 seconds after each application of the test flame; do not have a total flaming time of more than 50 seconds for the two flame applications of each set of five samples; do not have any specimens which burn completely up to the holding clamp which is positioned at the top of the specimen; do not have any specimens which ignite the cotton which is placed below the sample with flaming drips or particles; and do not have any specimens which glow longer than 30 seconds after removal of the test flame.

Other UL 94 classifications exemplify samples which are less flame retardant and self-extinguishing, and which have flaming drips or particles. These classifications are UL 94 V-1 and V-2. The polycarbonates within the scope of the present invention characteristically demonstrate those properties in the UL 94 V-0 classification.

The invention will further be illustrated but is not intended to be limited by the following Examples.

EXAMPLE 1

17.3 grams of sulfanilic acid and 5.3 grams of sodium carbonate are charged to a 500 ml single neck round bottom flask equipped with a magnetic stirrer, nitrogen inlet and a reflux condenser. 300 ml of dimethylformamide were added to the flask, the sulfanilic acid and the sodium carbonate in dimethylformamide were heated to reflux at which time most of the solid dissolved. The admixture was allowed to cool to room temperature and was stirred overnight. The sodium salt of sulfanilic acid precipitated from solution at room temperature giving a white fluffy solid. 28.6 grams of tetrachlorophthalic anhydride were charged to the flask with the sodium salt of the sulfanilic acid previously prepared. The admixture was heated and the solution became homogeneous. The solution was heated to 120° C. for 20 minutes and the tetrachlorophthalimido benzene sodium sulfonate (TCPS) began to precipitate. The admixture was then cooled at room temperature and filtered, leaving a precipitate. The precipitate was washed with 250 ml portions of dimethylformamide and a solid was obtained which was washed with 100 ml of ether. The recovered material was air dried overnight and subsequently vacuum dried. The material had a melting point in excess of 310° C.

The compound produced is of the structural formula:

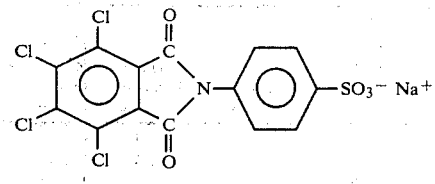

and its elemental analysis, compared with the theoretical makeup, is: (weight percent)

|  | C | H | N | S | Cl | Na |
|---|---|---|---|---|---|---|
| Theoretical | 36.30 | 0.87 | 3.02 | 6.90 | 30.66 | 4.97 |
| Actual | 36.06 | 1.14 | 3.10 | 6.90 | 30.27 | 4.72 |

EXAMPLE 2

A polycarbonate based upon bisphenol A having a melt flow rate of 7.4 g/10 min. in a powder form was tumble blended with sufficient tetrachlorophthalimido benzene sodium sulfonate (TCPS) to provide a concentration of the imide salt of 0.5% by weight based on the total weight of the polycarbonate resin.

The resin and salt admixture was first extrusion compounded and then molded into ⅛" specimens and 1/16" specimens for testing in accordance with the UL 94 test. The ⅛" specimen achieved a V-0 rating with an average burn time after withdrawal of the flame of 2.4 seconds. The 1/16" specimen also yielded a V-0 rating with an average burn time after the flame was withdrawn of 3.0 seconds. (See Table 1).

EXAMPLE 3

Example 2 was repeated except that 1% by weight of the tetrachlorophthalimido benzene sodium sulfonate (TCPS) was used instead of 0.5%. Testing in accordance with the UL 94 rating yielded a V-0 rating for the ⅛" specimen with an average burn time after the flame was withdrawn of 0.7 seconds. The 1/16" specimen yielded a V-0 rating with an average burn time of 2.3 seconds after the flame was withdrawn. (See Table 1).

TABLE I

| TCPS AS FLAME RETARDING ADDITIVE[a] | | |
|---|---|---|
| TCPS Concentration | UL 94 Rating | |
| (%) | ⅛" | 1/16" |
| 0.5 | V-0 (2.4)[b] | V-0 (3.0) |
| 1.0 | V-0 (0.7) | V-0 (2.3) |

[a] The additive is incorporated in a BPA based polycarbonate which also included crylite and PTFE.
[b] The numbers in parentheses denote the average burn time in seconds.

EXAMPLES 4 THROUGH 7

A polycarbonate resin based upon bisphenol A and phosgene having a melt flow rate of 7.5 g/10 min. was blended with varying amounts of tetrachlorophthalimido benzene sodium sulfonate (TDPS), extrusion compounded, molded and tested for melt flow, critical thickness and flame resistance. Table II shows the results of the test.

TABLE II

| Example | TCPS[a] Salt Concentration (wt. %) | Melt Flow[b] (g/10 min.) | Critical Thickness in Mils | Flame Resistance[c] (average burn time in seconds) |
| --- | --- | --- | --- | --- |
| control | 0 | 7.7 | 190 | V-2 |
| 4 | 0.1 | 7.5 | 163 | V-0 (2.9) |
| 5 | 0.17 | 7.5 | 153 | V-0 (1.9) |
| 6 | 0.42 | 7.7 | — | V-0 (1.7) |
| 7 | 0.37 | 7.7 | 153 | V-0 (1.6) |

[a]Tetrachlorophthalimido benzene sodium sulfonate.
[b]Measured according to ASTM D-1238.
[c]Measured according to UL-94 on ⅛" thick specimens.

EXAMPLE 8

The thermal stability of tetrachlorophthalimido benzene sodium sulfonate was evaluated by thermogravimetry. After 30 minutes at 300° C. a weight loss of 10% was noted. By comparison, n-phenylphthalimide completely volatilizes after 2.5 minutes at 300° C.

Thus, in accordance with the present invention the halogenated aromatic imide sulfonates of the invention when incorporated into the polycarbonates impart flame retardant characteristics thereto and have minimal weight loss upon heating at normal processing temperatures for polycarbonates.

Although the invention has been described with reference to specific materials and specific methods the invention is only to be limited so far as set forth in the accompanying claims.

What is claimed is:

1. The compound

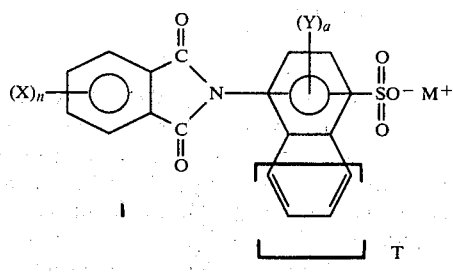

wherein X is a halogen,
n is an integer from 1 to 4,
Y is a lower alkyl having 1 to 4 carbon atoms, a halogen or a hydrogen atom,
a is an integer from 0 to 4,
M is an alkali metal, and
T is either 0 or 1.

2. The compound

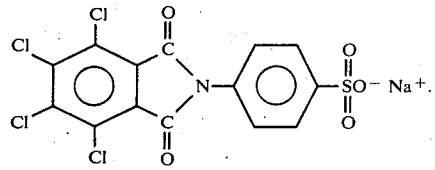

3. In the process of rendering thermoplastic aromatic polycarbonates flame resistant, the improvement comprising blending therewith 0.01 to 1% by weight the compound of claim 1 or claim 2.

4. In the process of rendering thermoplastic aromatic polycarbonates flame resistant, the improvement comprising blending therewith 0.1 to 0.75% by weight the compound of claim 1 or claim 2.

5. A thermoplastic aromatic polycarbonate comprising a polycarbonate resin and, from 0.01 to 1% by weight, the compound of claim 1 or claim 2.

6. A thermoplastic aromatic polycarbonate comprising a polycarbonate resin and, from 0.1 to 0.75% by weight, the compound of claim 1 or claim 2.

7. The thermoplastic aromatic polycarbonate of claim 5 or claim 6, wherein said polycarbonate resin is derived from bis-2-(4-hydroxyphenyl)propane.

8. A thermally stable flame retarding agent for polycarbonates, of the general formula:

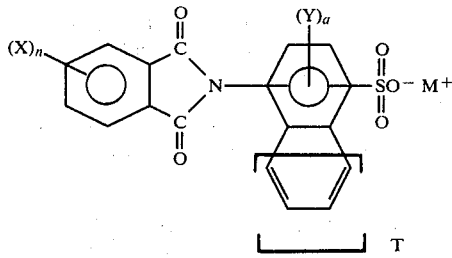

wherein X is a halogen atom, n equals 1 to 4, Y is a lower alkyl having 1 to 4 carbon atoms or a halogen atom, "a" is 0 to 4, M is an alkali metal and T is either 0 or 1 characterized in that it retains at least 90% of its weight after exposure to 300° C. for 30 minutes.

* * * * *